United States Patent [19]
Dukes et al.

[11] Patent Number: 4,573,475
[45] Date of Patent: Mar. 4, 1986

[54] RECEIVING RADIATION FROM LOOPS IN A COMMON PLANE FOR MONITORING HOSPITAL PATIENTS LEADLESSLY

[75] Inventors: John N. Dukes, Los Altos Hills, Calif.; Edwin B. Merrick, Stow, Mass.

[73] Assignee: Hewlett-Packard Company, Palo Alto, Calif.

[21] Appl. No.: 671,399

[22] Filed: Nov. 15, 1984

[51] Int. Cl.[4] ................................................. A61N 5/00
[52] U.S. Cl. ...................................... 128/653; 128/903
[58] Field of Search .............. 128/630, 631, 653, 661, 128/903

[56] References Cited
U.S. PATENT DOCUMENTS 3,561,430 2/1971 Filler, Jr. et al. ................ 128/661
3,683,389 8/1971 Hollis ................................ 128/631

FOREIGN PATENT DOCUMENTS 1279585 11/1961 France ............................... 128/631

Primary Examiner—William E. Kamm
Attorney, Agent, or Firm—Edward Y. Wong

[57] ABSTRACT

Output signals from a set of Faraday loops located in a common plane are combined selectively to simulate the output signals from a set of mutually orthogonal antennas. This arrangement and use of Faraday loops are especially suitable in a hospital environment for monitoring patients. Because of the availability of output signals from a set of equivalent orthogonal antennas, any danger of a gap in the monitoring of the patient is greatly minimized; the patient can be monitored regardless of the changing orientation of the patient with regards to the monitoring antennas.

8 Claims, 8 Drawing Figures

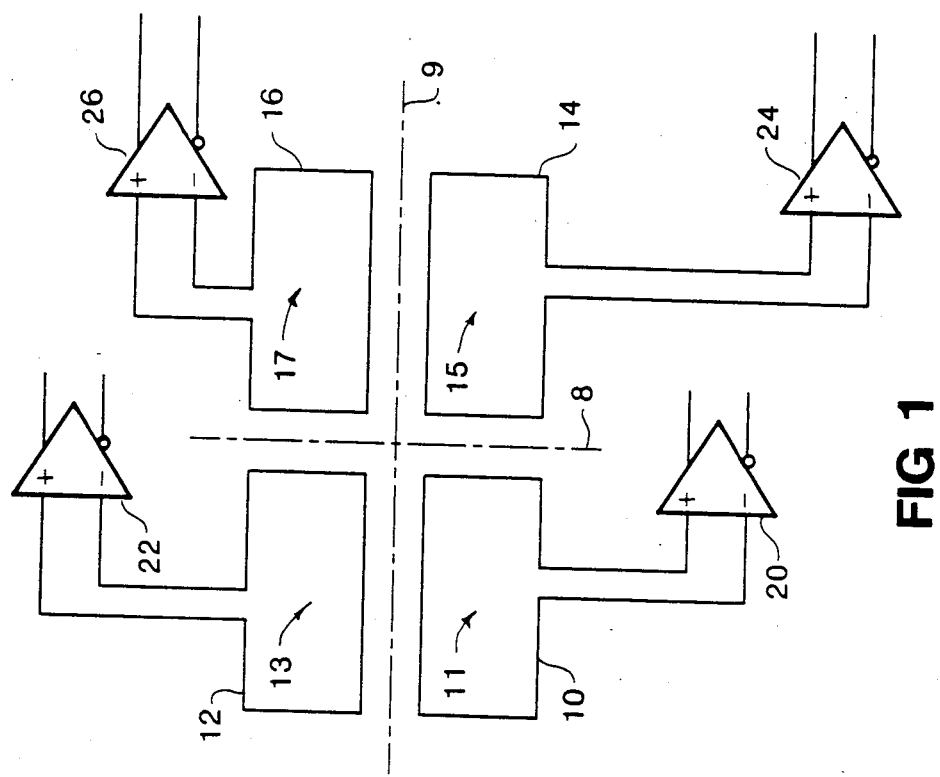

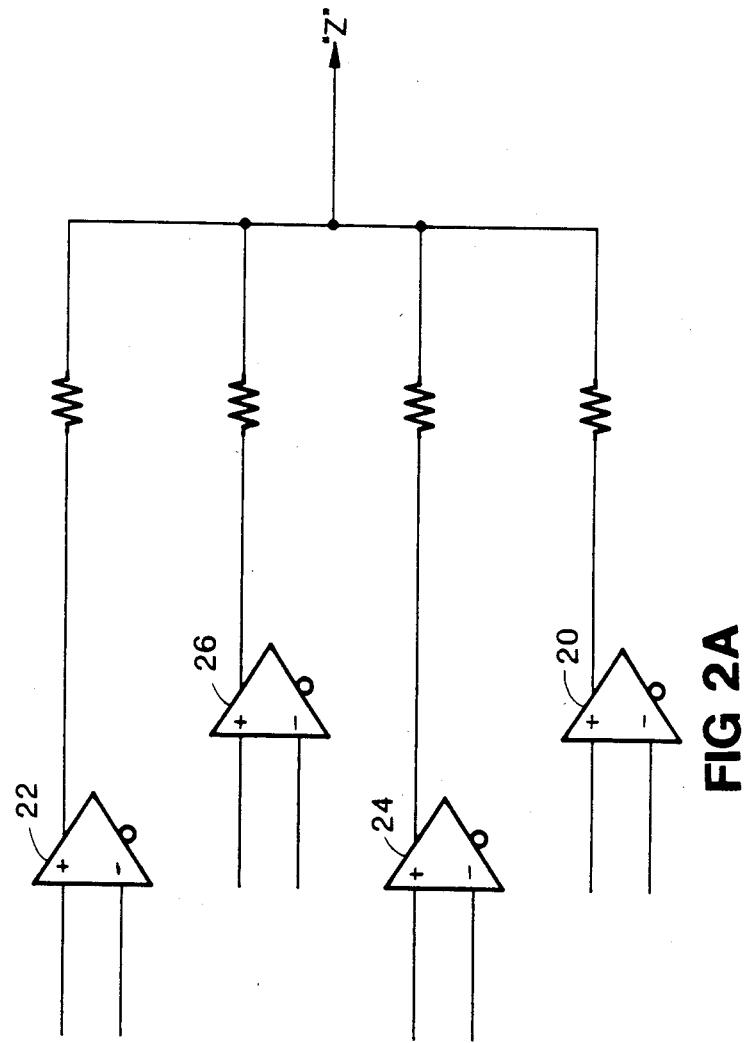

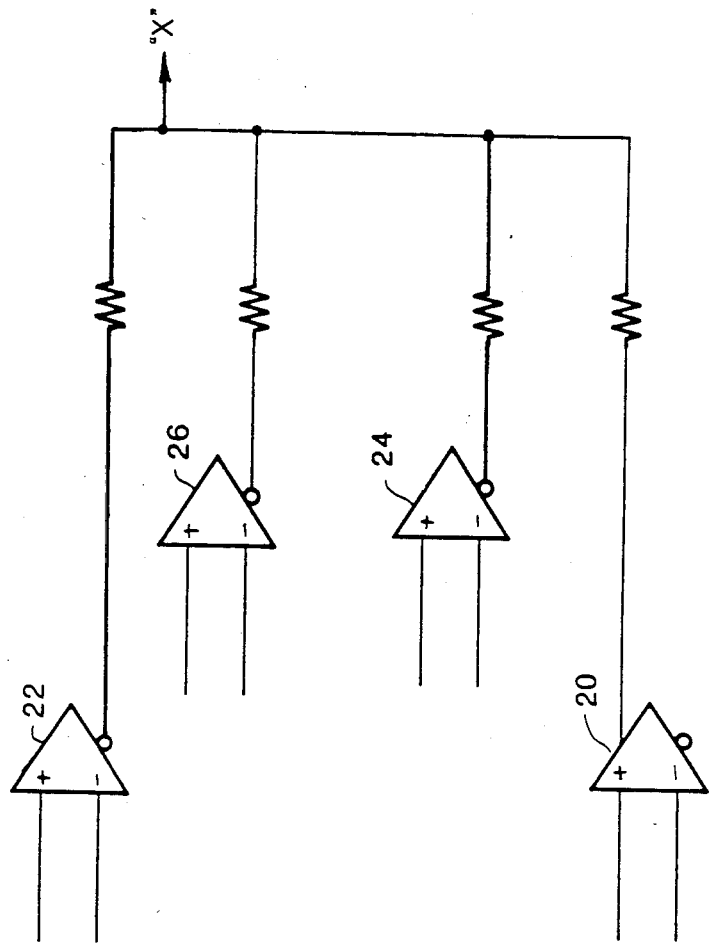

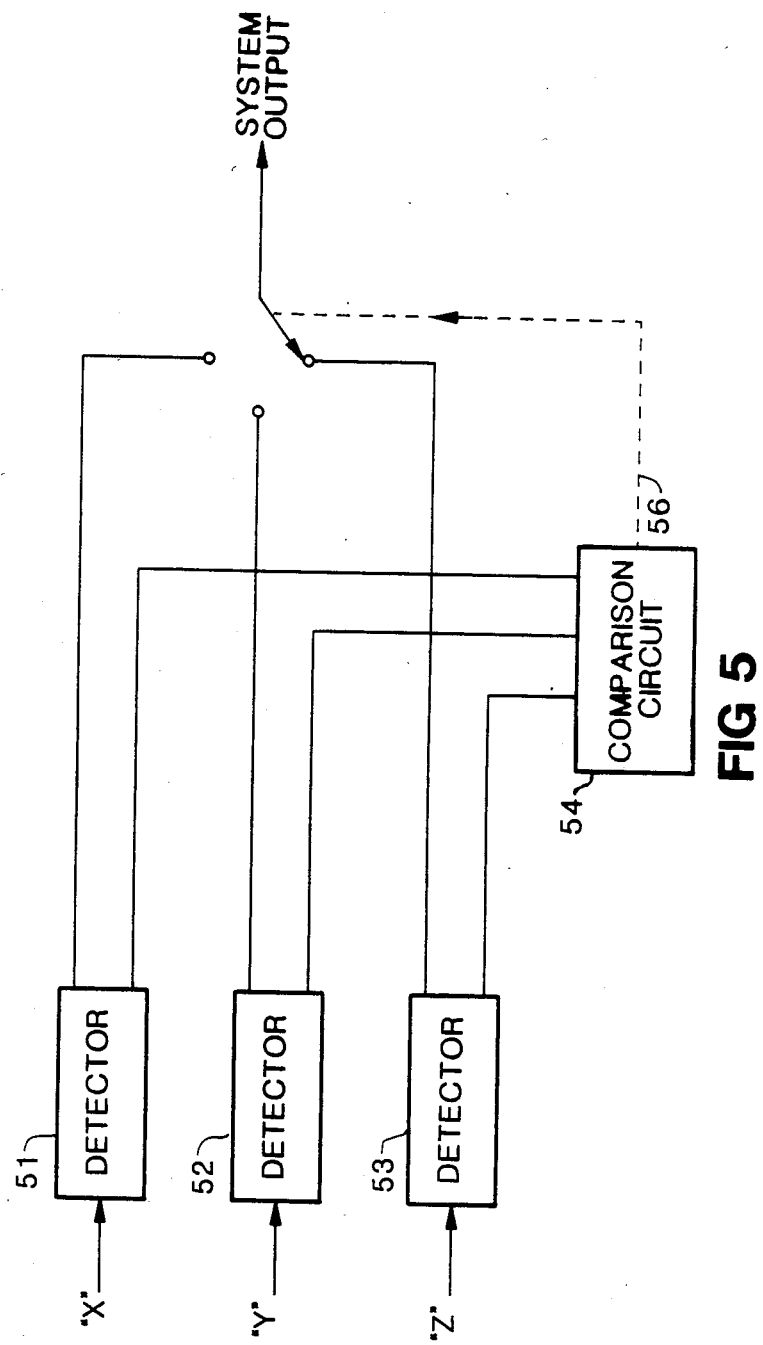

RECEIVING RADIATION FROM LOOPS IN A COMMON PLANE FOR MONITORING HOSPITAL PATIENTS LEADLESSLY

BACKGROUND AND SUMMARY

In the prior art, several methods of monitoring a bedridden patient in a hospital or a recuperation home for his vital signs have been used. Usually, these methods are implemented with leads or without leads. In the methods with leads, the patient has typically monitoring transducers attached to his body; these transducers in turn are electrically connected directly to pieces of equipment where transducer signals are read and interpreted. Because of the physical electrical connections between patient and equipment, the patient's movements are greatly impeded; the electrical connections tend to be entangled easily. Furthermore, there is ever present the danger of a malfunctioning piece of equipment causing an electrical shock to the directly connected patient. Therefore, the trend in patient monitoring has been toward leadless monitoring.

The leadless monitoring of patient in the prior art typically comprises a transmitter attached to the patient for transmission of signals showing the patient's vital signs and a receiver for collection and processing of these signals. Since the receiver is usually in close proximity, the transmission can be typically by very low frequency signals using a magnetic antenna. The advantages of low frequency transmissions have been adequately described in the prior art, e.g., by Andrzej B. Przedpelski, "'Near Field' Communication," *r.f. design*, March/April, 1980. But magnetically coupled antennas have one severe problem when applied to leadless monitoring: a magnetic antenna is not omnidirectional. Thus, there is an orientation of the transmitter with respect to the receiver which will not allow communication. In other words, there is an orientation creating a null between transmitter and receiver, and in patient monitoring where constant monitoring of the patient's vital signs is crucial, a null in communication can be fatal. With this method, the patient's movement, though not as much as with monitoring with leads, nevertheless is restricted again. And because of this disadvantage, low frequency leadless monitoring has not, if at all, been widely applied.

The method in accordance with the present invention overcomes the problem of null orientation with magnetic antenna coupling in leadless monitoring of patients and allows a patient greater freedom of movement than in the past. In accordance with the method, three equivalent orthogonally oriented magnetic antennas are obtained from selected combinations of output signals from four wire loop magnetic antennas in a plane. The combinations of signals received with these loop antennas are used for compound, or diversity, reception. Thus, no transmitting antenna orientation of the patient being monitored can cause a complete null in the receiver, since there is an equivalent antenna to receive the transmitted signals in three equivalent receiving axes and, being orthogonal to each other, there cannot be a simultaneous null in all three axes. Furthermore, the method in accordance with the invention allows all three receiving axes in one antenna to be located in one plane. This is especially desirable in the case of leadless hospital monitoring; the planar antenna can be easily laid down flat on a hospital bed under the mattress of the patient. The receiving antenna is then unobtrusive yet in close proximity to the patient to take advantage of magnetic coupling with very low frequency signals.

BRIEF DESCRIPTION OF THE DRAWINGS

FIG. 1 illustrates the preferred embodiment of the invention.

FIG. 2A shows the connection of four preamplifiers to obtain the equivalent of a magnetic antenna oriented along a z-axis.

FIG. 4A shows the connection of four preamplifiers to obtain the equivalent of a magnetic antenna oriented along an x-axis.

FIG. 5 shows the preferred embodiment of a diversity reception.

DETAILED DESCRIPTION OF THE INVENTION

Figure 2B:
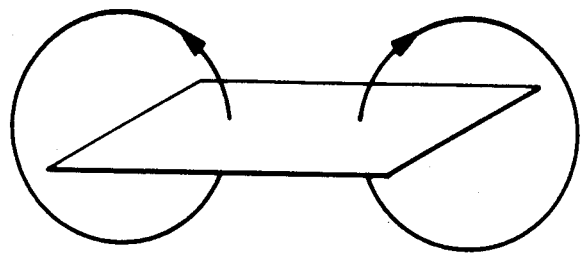
FIG. 2B shows the equivalent magnetic flux and loop orientation obtained with this connection.

In accordance with the preferred embodiment of the invention as illustrated in FIG. 1, four Faraday shielded wire loops 10, 12, 14, 16 are arranged in each of four quadrants 11, 13, 15, 17 on a plane 18, where the four quadrants are defined by one line 8 spanning north-south and another line 9 spanning east-west. For ease of reference to the four quadrants, they are defined as follows: first quadrant 11 as that spanning from 6 to 9 o'clock; second quadrant 13 as that spanning from 9 to 12 o'clock; third quadrant 17 as that spanning from 12 to 3 o'clock; and fourth quadrant 15 as that spanning from 3 to 6 o'clock. These loops are arranged in a plane so that they can be advantageously inserted under a mattress of a hospital patient for magnetically coupling hospital signals. These hospital signals are transmitted from the body of a patient, and they may represent the vital signs of the patient. Alternatively, these signals may indicate position or movement of the patient. Each loop 10, 12, 14, 16 is connected to a respective preamplifier 20, 22, 24, 26, where the received signals are amplified for further processing. The output signals of the preamplifiers 20, 22, 24, 26 are then selectively combined. The resultant signal from a selective combination is a signal equivalent to one received from one of three simultaneously operating antennas orthogonally oriented along three different axes. The resultant signal then may be read for transmitted information on, for example, vital signs, relative movement, or relative position of the patient.

To obtain a received signal that is equivalent to one from a first orthogal antenna, e.g., one oriented along the z-axis, the positive output signal of each of the preamplifers 20, 22, 24, 26 connected to the four wire loops 10, 12, 14, 16 in the plane 8 are combined together as shown in FIG. 2A. Since all the loops 10, 12, 14, 16 add, the received signal from this combination is equivalent to a signal for an equivalent loop antenna having a magnetic axis vertical to the plane 18 of wire loops 10, 12, 14, 16 as shown in FIG. 2B. This first equivalent antenna, then, is oriented along the z-axis.

Figure 3B:
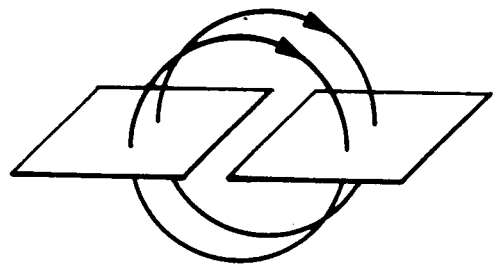
FIG. 3B shows the equivalent magnetic flux and loop orientation obtained with this connection.
Figure 3A:
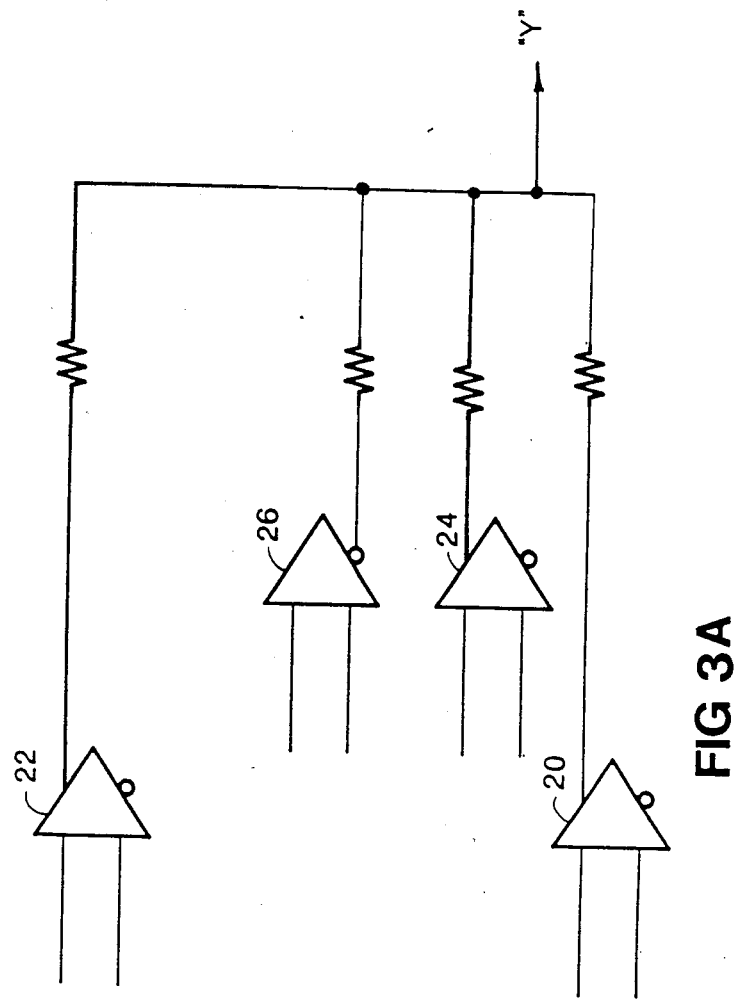
FIG. 3A shows the connection of four preamplifiers to obtain the equivalent of a magnetic antenna oriented along a y-axis.

If the positive output of the preamplifiers 20, 22 connected to the loops 10, 12 occupying the first and second quadrants and the negative output of the remaining two preamplifiers 24, 26 connected to the loops 14, 16 occupying the fourth and third quadrants are combined as shown in FIG. 3A, the signal resulting from the combination is equivalent to a signal received from a second equivalent axis. The magnetic flux for this second equivalent axis is from west to east as shown in FIG. 3B. This orientation will be the y-axis.

Figure 4B:
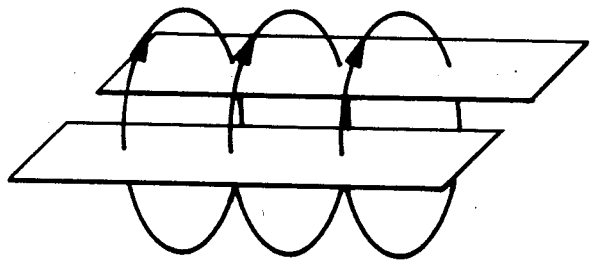
FIG. 4B shows the equivalent magnetic flux and loop orientation obtained with this connection.

To obtain a signal equivalent to one from a third equivalent axis, the positive output from the preamplifiers 20, 24 connected to the loops in the first and fourth quadrants and the negative output from the preamplifiers 22, 26 connected to the loops in the second and third quadrants are combined as shown in FIG. 4A. This combination results in greatest sensitivity to magnetic flux radiating south to north with respect to the plane 8 as shown in FIG. 4B. This orientation will be the x-axis.

As is evident from the above discussion, by selectively combining the output signals from the preamplifiers 20, 22, 24, 26, signals equivalent to those obtained from three orthogonally oriented antennas are realized with the preferred embodiment of the invention. Because of the orthogonal orientation of the equivalent antennas, at least one of the equivalent antennas will be receiving a signal transmitted; the orthogonal orientation precludes a simultaneous null of all three antennas. Hence, this type of leadless patient monitoring overcomes some of the disadvantages of other leadless monitors in the prior art.

A further refinement of the preferred embodiment is the implementation of a diversity reception circuit as shown in FIG. 5. The output signals representing the equivalent signals from a set of mutually orthogonal antennas are each detected by a detector circuit 51–53. A comparator circuit 54 having the detected outputs of each of the detector circuits 51–53 as inputs determines which of the detected outputs has the greatest amplitude, or strength. A control 56 from the comparator circuit 54 then controls an output switch 55 to direct the switch 55 to couple the detected signal with the greatest amplitude as the output of the system.

We claim:

1. A system for receiving electromagnetic radiation comprising:
   a plurality of electrically conductive wire loops in a substantially common plane, each of said plurality of electrically conductive wire loops producing a respective first signal in response to said electromagnetic radiation;
   a plurality of receiving means for receiving said respective first signals, each of said plurality of receiving means being connected respectively to one of said plurality of electrically conductive wire loops; and
   a plurality of combining means, each of said combining means being connected to said plurality of receiving means for selectively combining a plurality of said first signals to form an equivalent received signal from an equivalent antenna.

2. The system as in claim 1 wherein said plurality of electrically conductive wire loops comprises four loops, each of said four loops being situated in a different quadrant in said common plane.

3. The system as in claim 2 wherein said combining means further selectively combine said first signals to form a signal equivalently from one of three orthogonally oriented equivalent antennas.

4. The system as in claim 3 further comprising a switching means connected to said plurality of combining means for selecting one of a plurality of said equivalent received signals as an output signal.

5. The system as in claim 4, wherein said switching means comprises:
   a plurality of detector means, each of said plurality of detector means being coupled to each of said combining means for detecting said equivalent received signal from said combining means, and
   a comparison means coupled to each of said plurality of detector means for determining the strongest of said equivalent received signals detected for selection as an output signal.

6. A method of monitoring a non-ambulatory patient comprising:
   transmitting a signal from said patient;
   coupling said signal to a plurality of electrically conductive wire loops in a substantially common plane to provide received signals in said plurality of conductive loops; and
   processing said received signals.

7. The method as in claim 6, wherein said step of processing further comprises selectively combining said received signals to provide an information signal.

8. The method as in claim 6, wherein said step of coupling further comprises coupling said signal to a plurality of electrically conductive wire loops disposed in different quadrants in a substantially common plane.

* * * * *